(12) United States Patent
Purcell et al.

(10) Patent No.: US 10,219,643 B2
(45) Date of Patent: Mar. 5, 2019

(54) GLOVE DISPENSING APPARATUS AND GLOVE CARTRIDGE FOR USE THEREWITH AND GLOVE DISPENSING METHOD

(71) Applicants: David Scott Purcell, Chandler, AZ (US); John Robert Morris, Chandler, AZ (US)

(72) Inventors: David Scott Purcell, Chandler, AZ (US); John Robert Morris, Chandler, AZ (US)

(*) Notice: Subject to any disclaimer, the term of this patent is extended or adjusted under 35 U.S.C. 154(b) by 0 days.

(21) Appl. No.: 15/593,409

(22) Filed: May 12, 2017

(65) Prior Publication Data

US 2018/0000270 A1    Jan. 4, 2018

Related U.S. Application Data

(63) Continuation-in-part of application No. 15/228,225, filed on Aug. 4, 2016, which is a continuation of
(Continued)

(51) Int. Cl.
*A47G 25/90* (2006.01)
*A41D 19/00* (2006.01)
(Continued)

(52) U.S. Cl.
CPC ....... *A47G 25/904* (2013.01); *A41D 19/0068* (2013.01); *A61B 42/50* (2016.02); *A61B 42/40* (2016.02)

(58) Field of Classification Search
CPC ... A47G 25/904; A61B 42/50; A41D 19/0068
See application file for complete search history.

(56) References Cited

U.S. PATENT DOCUMENTS 3,695,463 A    10/1972  Weisker et al.
3,695,493 A *  10/1972  Karr ............... A47G 25/904
                                              2/162
(Continued)

OTHER PUBLICATIONS

International Search Report (PCT/ISA/210) issued in PCT Application No. PCT/US2012/035451 dated Jul. 6, 2012 (two (2) pages).
(Continued)

*Primary Examiner* — Andrew W Sutton
(74) *Attorney, Agent, or Firm* — Crowell & Moring LLP

(57) ABSTRACT

An apparatus for dispensing a disposable glove and applying it to the hand of a user in which a stream of air drawn into an enclosed glove applying chamber through a constricted opening aligned with the heel of the glove inflates the topmost glove in a stack of gloves in the chamber so that a user can readily insert his hand into the glove. After the user has donned the glove on the hand, a wall of the chamber is opened to permit the user to readily withdraw his hand from the glove applying chamber while the air flow which originally inflated the top-most glove is disrupted. Upon closures of the chamber wall, the re-established air flow automatically inflates the next lower glove in the glove stack to prepare the next glove for receipt of another hand. The apparatus alternatively or in addition includes a glove removal chamber arranged to remove a glove from a gloved hand using a stream of air drawn into the glove removal chamber.

13 Claims, 6 Drawing Sheets

Related U.S. Application Data application No. 14/114,658, filed as application No. PCT/US2012/035431 on Apr. 27, 2012, now Pat. No. 9,414,706.

(60) Provisional application No. 61/481,005, filed on Apr. 29, 2011.

(51) Int. Cl.
*A61B 42/50* (2016.01)
*A61B 42/40* (2016.01)

(56) References Cited

U.S. PATENT DOCUMENTS

| | | | |
|---|---|---|---|
| 4,002,276 A | 1/1977 | Poncy et al. | |
| 4,155,494 A | 5/1979 | Poncy et al. | |
| 4,889,266 A * | 12/1989 | Wight | A61B 42/50 206/278 |
| 4,915,272 A | 4/1990 | Vlock | |
| 5,058,785 A * | 10/1991 | Rich | A47G 25/904 223/111 |
| 5,078,308 A | 1/1992 | Sullivan | |
| 5,868,290 A | 2/1999 | Green, Sr. et al. | |
| 6,053,380 A | 4/2000 | Sherrod | |
| 6,435,888 B1 | 8/2002 | Reed, Jr. | |
| 6,832,708 B2 | 12/2004 | Sinai | |
| 6,932,253 B2 | 8/2005 | Sato | |
| 7,377,410 B1 | 5/2008 | Webb | |
| 8,651,323 B2 | 2/2014 | Balkin et al. | |
| 2014/0305974 A1 | 10/2014 | Purcell et al. | |
| 2017/0014198 A1* | 1/2017 | Gravlee | A61B 42/50 |
| 2017/0196645 A1* | 7/2017 | Ozkarsli | A61B 46/10 |

OTHER PUBLICATIONS

International Preliminary Report on Patentability (PCT/IB/373) issued in PCT Application No. PCT/US2012/035451, including Written Opinion (PCT/ISA/237) dated Nov. 7, 2013 (five (5) pages).

* cited by examiner

GLOVE DISPENSING APPARATUS AND GLOVE CARTRIDGE FOR USE THEREWITH AND GLOVE DISPENSING METHOD

CROSS REFERENCE

This application is a continuation-in-part of U.S. application Ser. No. 15/228,225, filed Aug. 4, 2016, which is a continuation of U.S. application Ser. No. 14/114,658, filed Jun. 26, 2014, now U.S. Pat. No. 9,414,706, which is a National Stage application of PCT International Application No. PCT/US2012/035431, filed Apr. 27, 2012, which claims priority to Provisional Application No. 61/481,005, filed Apr. 29, 2011, the disclosures of which are expressly incorporated by reference herein.

BACKGROUND OF THE INVENTION

In food service and food handling industries, public health considerations have led to rules mandating that workers wear gloves when handling food. Corresponding requirements also exist in other industries. In sandwich shops and similar establishments where workers successively serve a series of customers, it may be required in order to prevent cross-contamination that the workers don a new set of gloves for each customer. As a result, there is a need for inexpensive gloves which are readily disposable. Such gloves are commonly made from two layers of polymeric film cut to the general shape of a hand and heat sealed around the periphery to from an enclosure for the hand.

In many cases, however, such gloves can be difficult to apply. The thin polymeric films from which the gloves are made can be difficult to grip. Static charges or natural adhesion may cause the layers to adhere to each other, thereby making it difficult for a user to open the glove for insertion of the hand. Service delays which occur as workers struggle to put on a new set of disposable gloves reduce the overall efficiency of food service establishments. It would be highly desirable for such businesses if an apparatus were available to facilitate rapid and reliable donning of a new disposable glove by the personnel of the establishment.

Efforts have been made in the past to devise glove applying devices, particularly for surgical gloves. Such devices, however, have tended to be complicated and/or to involve complex structural arrangements, such as tight peripheral seals, unsuited to the dispensing of lightweight and inexpensive food service gloves. For example, U.S. Pat. No. 3,695,463 discloses a system in which an individual glove is inserted into a vacuum-generating machine, where each individual glove must be first handled and a seal between the wrist opening of the glove and the vacuum-generating machine must be created. The need to individually handle the gloves and to positively seal the wrist region of the glove to permit a strong vacuum to be generated (such as by clamping the wrist region of the glove on the vacuum-generating machine, rolling the wrist region over a rim of the vacuum-generating machine, or providing a rigid ring about the glove wrist area to support the glove when located in the vacuum-generating machine) is a problem common to a number of such designs, for example, as disclosed in U.S. Pat. Nos. 4,002,276, 4,155,494, 4,889,266, 4,915,272, 5,058,785, 5,078,308, 5,868,290, 6,053,380, 6435,388, 6,832, 708 and 6,932,253.

SUMMARY OF THE INVENTION

It is therefore an object of the invention to provide an improved apparatus for dispensing and applying a glove to the hand of a user.

Another object of the invention is to provide an apparatus for dispensing and applying a glove to the hand of a user which is structurally uncomplicated, yet reliable and can be produced at reasonable cost.

A further object of the invention is to provide an apparatus for dispensing and applying a glove to the hand of a user which avoids the need for the user to fumble with the glove and facilitates rapid and convenient application of a glove.

An additional object of the invention is to provide an apparatus for dispensing and applying a glove to the hand of a user which can be used repeatedly in rapid succession.

It is also an object of the invention to provide as an article of manufacture a glove cartridge or stack of gloves adapted to be dispensed and applied to the hand of a user by the aforedescribed glove dispensing and applying apparatus.

Another object of the invention is to provide an apparatus which does not rely on a completely sealed container in order to enable the opening of a glove to permit insertion of a hand.

A further object of the invention is to provide a method for donning a glove in which individual gloves are inflated by the use of gas flow around the glove so as to present the open heel of the glove (i.e., the glove wrist opening) to a user for donning, without the need for sealed containers or pre-mounting of the glove on a glove-holding apparatus.

These and other objects of the invention have been achieved by providing a glove opening and dispensing machine in which air flow is developed over a top glove in a stack of one or more gloves in a manner which causes the top glove to be expanded open by the air flow without the assistance of any sort of wrist-opening supporting device or the establishment of a sealed vacuum compartment. As a result, the operator may quickly and simply insert a hand into the glove and immediately remove the gloved hand without needing to contact any surface of the glove other than its interior.

The gloves may be arranged in a stack having relatively small tabs on the lower edge of the glove wrist opening which provide for contact and retention on at least one of the next lower glove in the stack and the stack itself. The retention may result from a variety of approaches, such as the presence of an adhesive on the lower face of a connecting tab or by use of glove stacking tabs on the heel of the glove, as long as the approach: (i) permits the top glove on the stack to be inflated by gas flow while the tab or other stacking aid retains the top glove on the stack and helps to keep the next glove down in the stack from opening in response to the air flow; (ii) the top-glove's heel tab is readily released from the stack as the operator removes their gloved hand from the machine; and (iii) removal of the top glove and its tab or other stacking aid permits the next glove in the stack to immediately inflate in the air flow so as to be quickly ready for the next operator hand insertion.

Further objects of the invention have been achieve by providing a method for donning gloves including the steps of operating a gas flow generating source to create a gas flow across at least a top glove in a stack of gloves in an unsealed glove inflation chamber, inserting a hand into the top glove which has inflated upon establishing the gas flow past the top glove in the glove inflation chamber, moving the top glove with the hand away from the stack of gloves to separate the top glove from the stack of gloves. The method for donning gloves further may include the step of, after inserting the hand into the top glove, disrupting the gas flow in the glove inflation chamber, and the step of disrupting the gas flow to facilitate removal of the gloved hand by at least one of operating a bypass valve to disrupt flow into an opening of the glove inflation chamber, operating an outlet valve to disrupt flow out of an outlet opening of the glove inflation chamber, and turning off the gas flow generating source by at least one of manual and automatic actuation of a power switch of the gas flow generating source.

An additional object of the present invention is to provide an apparatus that permits automatic and/or touchless removal of gloves, such as those dispensed in the above-identified apparatus. One embodiment of the glove removal apparatus includes a chamber with inlet, outlet and side wall surfaces configured such that when a gloved hand is inserted through the inlet, the glove is automatically removed by a pressure difference between the interior and exterior surfaces of the glove generated by a vacuum source accelerating air flow passing from the ambient environment into the chamber along the exterior surface of the glove.

Further advantageous refinements and preferred aspects of the invention will be apparent from a consideration of the following description and claims and the accompanying drawing figures.

BRIEF DESCRIPTION OF THE DRAWINGS

The invention will be described in further detail hereinafter with reference to illustrative preferred embodiments shown in the accompanying drawing figures, in which.

DETAILED DESCRIPTION

Figure 1:
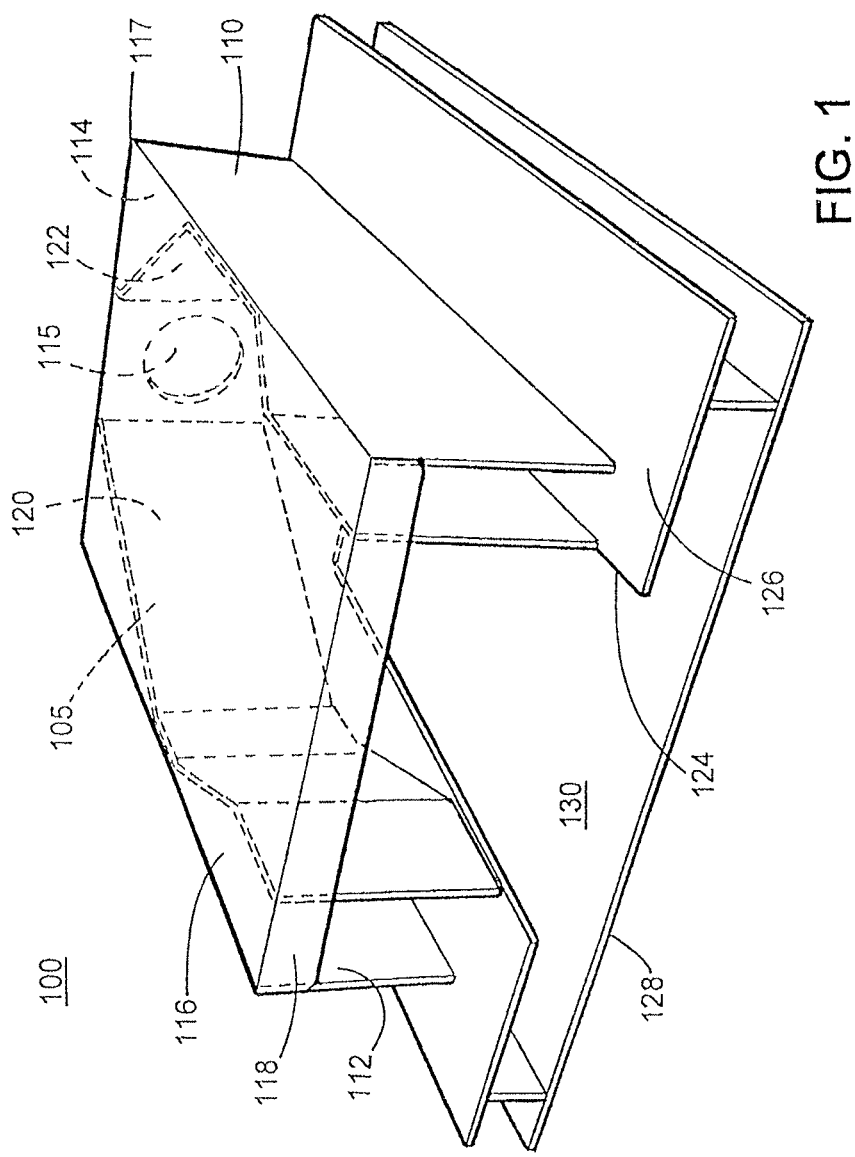
FIG. 1 is a perspective view of an illustrative embodiment of a glove dispensing and applying apparatus according to the invention in which interior components are depicted in broken lines.

FIG. 1 illustrates a view of a glove dispensing apparatus 100 in accordance with an embodiment of the present invention. In this arrangement, a glove inflating chamber 105 is formed within a box-shaped structure having side walls 110, 112, rear wall 114 and a hinged lid 116. The rear wall 114 has a gas outlet opening 115 (here, a round port) through which a gas (in this embodiment, air) is drawn during operation of the glove dispensing apparatus 100, as discussed further below. The hinged lid 116 pivots in the vicinity of the rear wall 114 about axis 117, acting as a valve which alters the gas flow through the glove inflating chamber 105 as the lid 116 is opened and closed. The hinged lid 116 also includes a front panel 118 which helps control air flow during operation of the glove dispensing apparatus 100, as discussed further below. The glove inflating chamber 105 also includes internal air flow control walls 120, 122 which are shaped to generally closely conform to an outer profile of a glove.

In this embodiment, the glove inflating chamber 105 is located about a cutout 124 in the floor plate 126 upon which the ox-shaped glove inflating chamber 105 is located. The floor plate is located above a base plate 128, thereby defining a recessed platform area 130 in which a stack of gloves may be placed in preparation for glove donning (stack not illustrated for clarity, see example stack details in FIGS. 5, 6, 6A).

Figure 2:
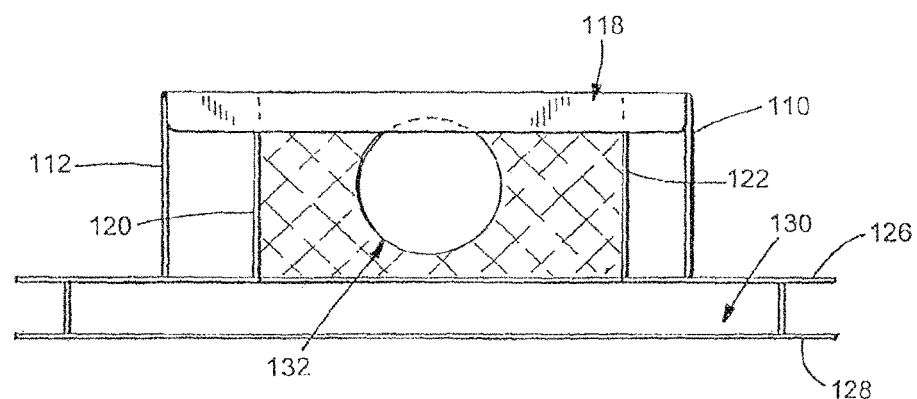
FIG. 2 is a front elevation view of the apparatus of FIG. 1.
Figure 3:
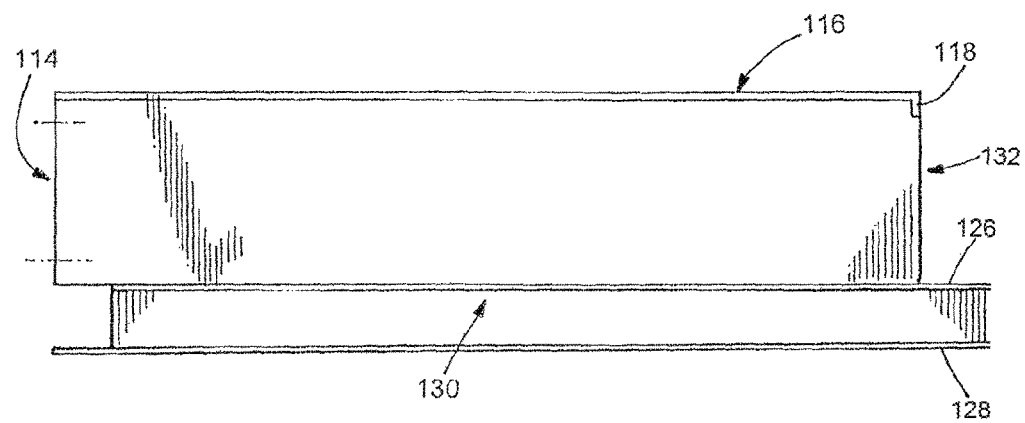
FIG. 3 is a side elevation view of the apparatus of FIGS. 1 and 2.

FIGS. 2 and 3 show front elevation and side elevation views, respectively, of the FIG. 1 embodiment. The FIG. 2 view in particular shows the relatively constrained size of the front opening 132, a feature which enhances air flow about the open end of the top glove in the stack of gloves. The configuration of the front opening 132 also illustrates a feature of the present invention, the lack of reliance on a completely sealed operating environment to ensure adequate inflation of the glove for hand insertion, unlike the case in the patents identified above. This greatly reduces the design complexity and operational issues, as there is no need for installation or other handling of the gloves in order to prepare them for mounting in a sealing fixture, as in prior art glove inflation machines.

Figure 4:
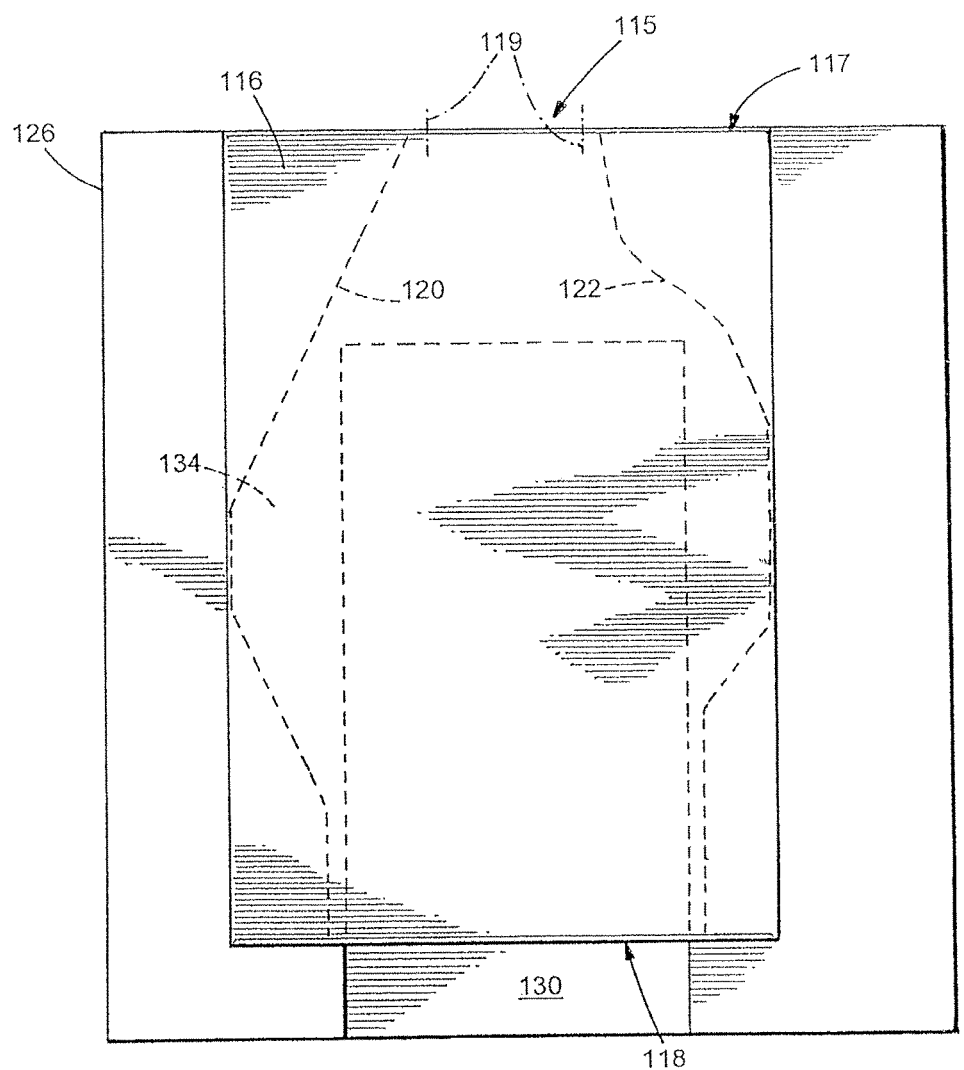
FIG. 4 is a top view of the apparatus of FIGS. 1-3.

FIG. 4 is a top view of the FIG. 1 apparatus, showing the generally glove-shaped region 134 between internal air flow control walls 120, 122 within glove inflation chamber 105. The shape of the generally glove-shaped region 134, corresponding generally to a plan view profile of the stack of gloves, is provided to maintain consistent air flow velocity around the top glove in the stack of gloves to help maintain the inflated glove shape during glove donning.

Figure 5:
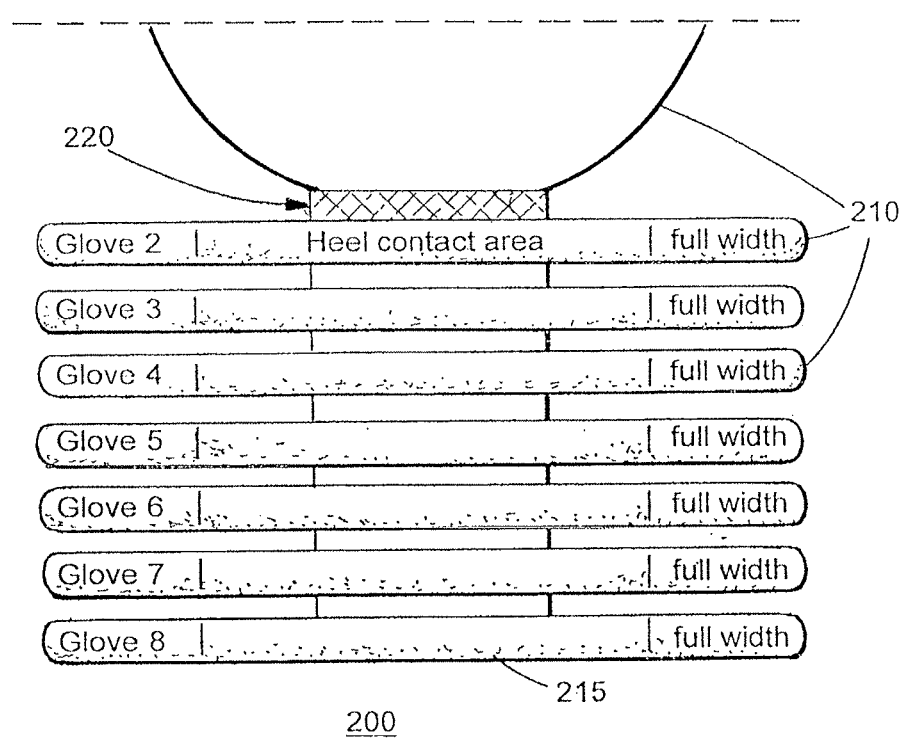
FIG. 5 is an enlarged detail end view of the stacking arrangement of a series of gloves in a glove cartridge adapted for use in the apparatus of the invention.
Figure 6:
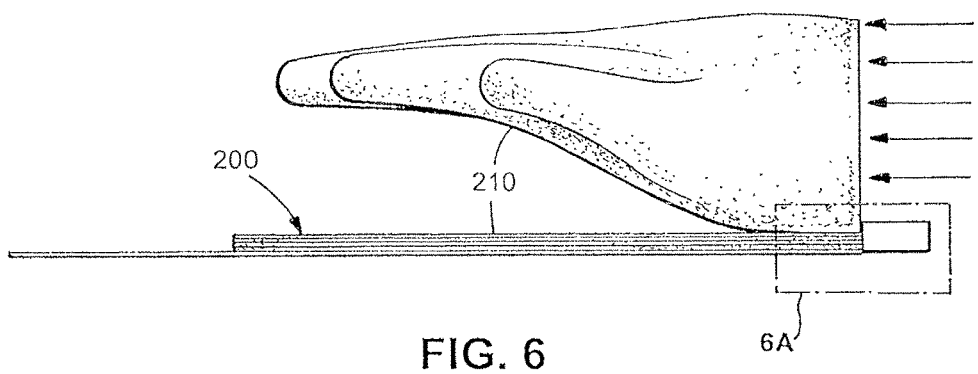
FIG. 6 is a side view of a glove cartridge in the apparatus of the invention with the topmost glove inflated and ready to receive the hand of a user.
Figure 6A:
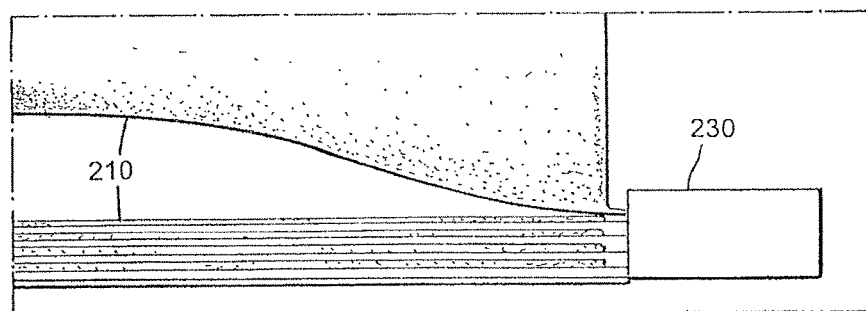
FIG. 6A is an enlarged detail view of a portion of the glove cartridge of FIG. 6 in the area identified by rectangle A showing how the topmost glove prevents inflation of the underlying gloves.

Details of an arrangement of a stack of gloves well suited to use with the FIG. 1 apparatus embodiment of the present invention are shown in FIGS. 5, 6 and 6A. FIG. 5 shows an elevation view of a stack 200 of gloves 210. In this embodiment of the stack of gloves, the gloves 210 are stacked on top of one another. As seen in the FIG. 5 elevation view, the gloves 2-7 in the stack of gloves 200 have a full width which is accommodated in the generally glove-shaped region 134 of the apparatus 100, while the width of the front opening 132 of the glove inflation chamber 105 generally corresponds to the width of the heel of the gloves 215.

In this embodiment of the stack 200, there is no connection between the gloves 210 except for a relatively small glove heel contact area 220 located within the width of the heel of the gloves 215. This heel contact area 220 is located only on a lower portion of the glove heel opening, and is provided to act as an anchor for the top glove. This anchor holds the top glove in the stack in place while the glove is being inflated, yet does not offer-significant resistance to separation of the top glove from the stack 200 after the user has inserted a hand into the top glove and pulled the glove out of the apparatus 100. The width of the heel contact area may vary, so long as sufficient contact is provided to secure the glove to the glove stack until a hand is inserted and the glove is removed, while still allowing the upper surface of the topmost glove to rise enough to allow a hand sufficient room to enter 'the glove. In a preferred embodiment, the secured portion in the heel contact area 220 may extend along from 10 to 50% of the glove width, and further along from 15 to 35% of the glove width.

A similar heel contact area is provided between each of the gloves in the glove stack 200. One of ordinary skill will recognize that there are many ways to provide such a connection between the heel contact area 220 and either the next lower glove or the rest of the glove stack while still providing for easy removal of the top glove from the stack. For example, the use of a low-adhesion adhesive over a small area would serve these functions, as would use of an easily torn-off tab at the heel of the glove, the use of a thermal bonding process such as thermal fusion, or the use of a series of interlocking molded surface features.

This glove stacking approach provides a low-cost approach to glove preparation for inflation, and greater hygiene as the individual gloves do not have to be handled (and thus potentially contaminated by the handler) in order to prepare the gloves for inflation.

In operation, the embodiment illustrated in FIGS. 1-6A functions as follows.

First, a glove stack 200 is placed in the recessed platform area 130, aligned with the generally glove-shaped region 134 and with the glove heel region at the front opening 132 of the glove inflation chamber 105. The lid 116 is lowered to close off the top of the glove inflation chamber 105, and an air flow generating source 119 is turned on, either manually by the operator or automatically, such as when triggered by a switch as the lid 116 is closed or when the presence of an approaching hand is detected by a proximity sensor.

The air flow generating source may be any device which creates a sustained air flow through the glove inflation chamber 105, such as a blower with its suction side connected to rear port 115. Because a high vacuum need not be established in the glove inflation chamber 105, the blower which creates the air flow need not be a high-power vacuum pump, but instead needs only establish a sufficient air flow to accomplish the top glove lifting action described below. This permits the use of a lower power and less costly blower than was often needed in the prior art sealed vacuum-based glove inflation machines.

When the air flow generating source is turned on, a relatively high velocity air flow is established in the glove inflation chamber 105, with the air entering the chamber via constrained front opening 132 and being drawn out of the rear of the chamber via port 115. The relatively high air flow velocities are achieved, despite the relatively low power of the air flow generating source, as a result of the close confirmation of the walls 120, 122 around the sides of the top glove, and with the assistance of lid 116's front panel 118, which reduces the cross-sectional area of the front opening 132 above the glove stack 200.

One of ordinary skill will recognize that in accordance with Bernoulli's law, as the air flow velocity over and around the top glove increases, there is a corresponding drop in the local air pressure around the exposed surfaces of the top glove. One of ordinary skill will also recognize that due to the heel opening of the glove facing the incoming air flow, a pressure difference is created between the interior of the top glove and the exterior of the glove, causing the upper surface of the glove to begin to rise automatically, i.e., without any contact between the operator and the glove exterior, and thereby preserving the hygiene of the glove.

The top glove continues to inflate in the glove inflation chamber 105 until it reaches its fully inflated state as shown in FIG. 6. The top glove remains fully inflated as long as the air flow generating source is operating to maintain the air flow through the chamber and the hinged lid 116 remains closed. As shown in FIG. 6A, the top glove is retained in place on the top of the glove stack 200 by its connection to the next lower glove at the glove heel contact area 220. In the FIG. 6A illustration, the heel contact area 220 of the top glove is connected to the next lower glove (and the remaining gloves in the glove stack 200) by a common tear-off block 230. Because the heel contact area 220 of the topmost glove in the stack covers the heel opening of the next lower glove in the stack, no significant amount of air may enter the next lower glove through its wrist opening. As a result, the next lower glove is constrained from inflating while the top glove is still attached to the stack of gloves 200.

Once the top glove is inflated, the operator need only insert their hand into the standing-open glove, and once fully inserted, simply lift the lid 116 (thereby disrupting the air flow in the closely-conforming glove inflation chamber 105) to allow them to lift their gloved hand out of the chamber. Because the strength of the retention feature between the top glove and the next lower glove in the glove heel contact area 220 is relatively weak (i.e., strong enough to retain the top glove in the face of the relatively small aerodynamic forces created by the air flow through the chamber 105, but weak enough to be easily released as the operator lifts their hand out of the chamber), the operator may very quickly don the topmost glove in the stack 200 and remove their gloved hand from the glove dispensing apparatus 100 very rapidly. This is in contrast to some prior art machines which required significant set-up time and time-consuming multiple-step operations to install the glove into its held-open position and to then extract the gloved hand and prepare the machine for inflation of the next glove.

Once the operator's freshly-gloved hand is removed from the glove dispensing apparatus 100, the operator may turn the air flow generating source off. Alternatively, the operator may lower the hinged lid 116 back down over the glove inflating chamber 105. IF the lid 116 is lowered after turning off the air flow generating source, the apparatus will be in a condition where when turned back on, the next lower glove in the glove stack 200 (now the new top glove) will be automatically inflated in response to the re-established air flow through the glove inflating chamber 105.

Alternatively, if the air flow generating source remains turned on, when the lid 116 is lowered back down to again close off the top of the glove inflation chamber 105, the next lower glove in the glove stack 200 (now the new top glove) will immediately begin to inflate as the air flow through the front opening 132 and the glove conforming-shaped portions the glove inflating chamber 105 is begins to be restored. Thus, by a very simple operation which in some embodiments requires at most only a few seconds, the operator may nearly instantly don one or two fresh, untouched hygienic gloves and immediately return to their work tasks.

Figure 7B:
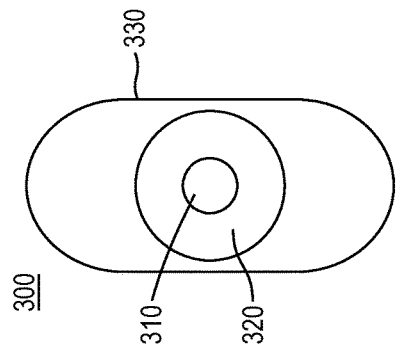
FIGS. 7A-7C are top, front and side views, respectively of a glove removal apparatus in accordance with an embodiment of the present invention.
Figure 7A:
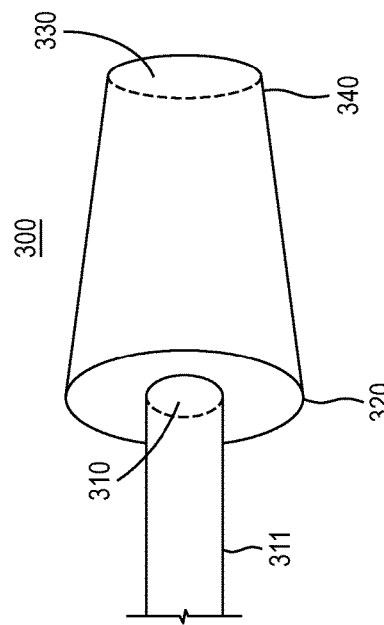
Figure 7C:
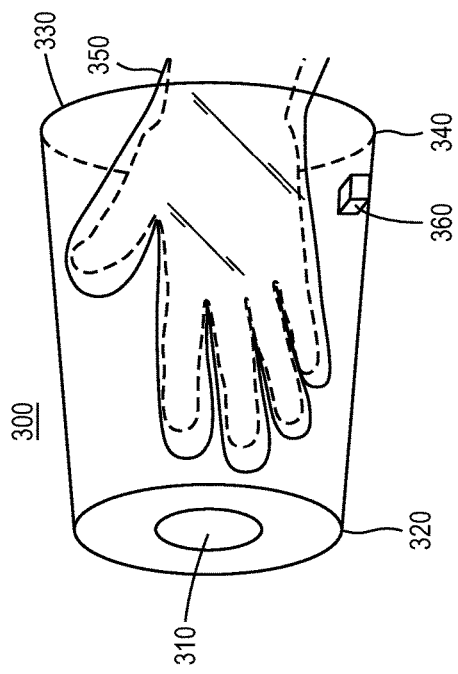

In further embodiments of the present invention, variations of the above-described apparatus may also provide the ability to remove a glove from a user's hand. In the embodiment shown in FIGS. 7A-7C, a glove removal chamber 300 includes an outlet 310 at an outlet end 320, and an inlet 330 at an inlet end 340. FIG. 7A shows a view of chamber 300 from above, while FIG. 7C shows an oblique side view. FIG. 7B is a view from the inlet end 340 of the chamber 300, looking toward the outlet end 320 and the outlet 310.

As shown in FIGS. 7B and 7C, the inlet 330 is shaped to generally conform to the cross-section of an extended hand, with sufficient annular clearance to permit a gloved hand 350 to be inserted through the inlet 330 into the interior of the chamber 300, preferably without the glove contacting the inlet or the walls of the chamber. In this embodiment the chamber 300 tapers from the inlet end 340 to the outlet end 320. In operation, when vacuum from an vacuum source (such as a vacuum pump connected to the outlet 310 by hose 311) is applied to the chamber via outlet 310, the velocity of the ambient air entering the inlet 330 increases. When a gloved hand is inserted into the inlet 330, the available air flow cross-sectional area through the inlet is substantially reduced, resulting in a further increase in the entering air flow velocity, and a consequent reduction in the pressure in the region around the outer surface of the glove. In turn, because the air pressure within the glove adjacent to the user's hand is higher that outside the glove (due to the open end of the glove at the user's wrist still being exposed to the ambient air pressure), the pressure difference between the inside and outside of the surfaces of the glove tends to cause the glove to be drawn off the user's hand toward the chamber outlet 310. Experiments have shown that at even moderate levels of vacuum at the outlet 310, a glove may be nearly instantaneously removed from a hand as the gloved hand is inserted through the inlet 330 into the chamber 300, without either contact with the wall of the chamber 300 or further manipulation of the hand.

As the glove is stripped from the user's hand in a non-contact manner, the high velocity air flow through the annulus between the hand and the periphery of the inlet 330 typically causes a suitably thin and flexible glove to collapse into itself as the glove leaves the hand, facilitating its passage through outlet 310 and hose 311 toward the vacuum source. Removed gloves may accumulate in a collection chamber (not illustrated) between the outlet 310 and the vacuum source for subsequent collection and recycling or disposal (for example, in the same manner that debris is accumulated in the collection bag of a household vacuum cleaner).

The vacuum source may be actuated by a manual switch either at or remote from the chamber 300. For greater user convenience, the vacuum source may be triggered to begin and end operation by the use of a device such as a microswitch or a sensor 360 (including but not limited to infrared or acoustic sensors) that senses the presence of a hand entering the chamber 300 and starts the vacuum source. Alternatively, the vacuum source may run continuously.

A glove removal chamber such as chamber 300 may be mounted with an embodiment of the glove dispensing apparatus of the present invention, for example adjacent to or on top of the glove dispensing portion of the apparatus, and share the same vacuum source to lower costs. Alternatively, the glove removal chamber may be embodied as a stand-alone apparatus, preferably in a small footprint arrangement which enables convenient placement of the apparatus close to a user's work area.

Figure 8:
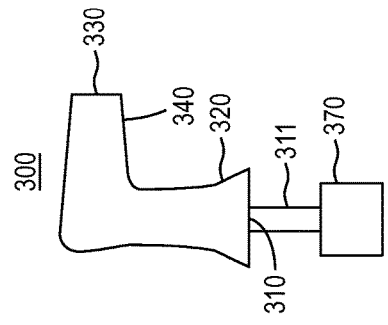
FIG. 8 is a cross-section elevation view of another embodiment of a glove removal apparatus in accordance with an embodiment of the present invention.

The glove removal apparatus of the present invention is not limited to the example apparatus configuration illustrated in FIGS. 7A-7C. For example, the shape of the inlet, the outlet and the side walls may be varied as desired, as long as the required amount of glove-removing air flow velocity and differential pressure is generated at the inlet. Nor is the invention limited to a linear inlet-to-outlet alignment, but includes any non-linear chamber which makes use of the operating principles of the present invention. For example, as illustrated in the cross-section elevation view in FIG. 8, the outlet 310 may be located at the bottom of an L-shaped chamber 300, such that a glove removed from a gloved hand inserted into a horizontally-aligned inlet 330 may be drawn by the vacuum source 370 down into vertically-aligned outlet 310 and hose 311.

Similarly, the invention is not limited to embodiments that require a removed glove to exit the chamber through the same aperture as that to which the vacuum source is connected. For example, the glove removal chamber may be shaped with the vacuum source aperture located both relatively far away from the inlet and in a relatively large region of the chamber, such that by the time a removed glove arrives in the large region the local air flow velocity is low enough to permit the glove to drop into a lower accumulation chamber without being drawn into the vacuum source aperture.

The foregoing description and examples have been set forth merely to illustrate the invention and are not intended to be limiting. For example, rather than lifting the lid 116 of the glove inflating chamber 105 to disrupt the air flow in the chamber, a closure valve which blocks the flow of gas out of the outlet port 115 may be used to reduce the air flow in the chamber to the point that the air flow will not inflate the top-most glove in the glove stack 200. Similarly, rather than providing an apparatus having a single glove inflation chamber, multiple chambers (such as a left chamber and a right chamber) may be provided to permit simultaneous donning of gloves on both hands of an operator. Since modifications of the describe embodiments incorporating the spirit and substance of the invention may occur to persons skilled in the art, the invention should be construed broadly to include all variations within the scope of the appended claims and equivalents thereof.

The invention claimed is:

1. A glove removal apparatus comprising:
an enclosed glove removal chamber having:
an unsealed hand insertion inlet at an inlet end of the chamber,
an outlet opening at an outlet end of the chamber configured to permit air within the chamber to flow out of the chamber,
wherein the unsealed hand insertion inlet is configured to provide an annular space between a gloved hand inserted into the unsealed hand insertion inlet and an inner side wall of the chamber adjacent to the unsealed hand insertion inlet such that a flow of air from the unsealed hand insertion inlet to the outlet opening configured to remove a glove from the gloved hand while the hand is within the enclosed glove removal chamber.

2. The glove removal apparatus according to claim 1, further comprising:
an air flow generating device configured to draw air into the chamber through the annular space at an air flow rate sufficient to remove the glove from the gloved hand.

3. The glove removal apparatus according to claim 2, wherein
the air flow generating device is a vacuum-producing fan.

4. The glove removal apparatus according to claim 2, wherein
the air flow generating device is coupled to the outlet opening in a manner permitting the air flow generating device to withdraw the air entering the chamber through the annular space from the chamber.

5. The glove removal apparatus according to claim 4, wherein
the glove removal chamber includes a removed glove collection region, and
the outlet opening and the removed glove collection region are sized and located relative to one another such that the glove removed from the gloved hand does not pass through the outlet opening.

6. The glove removal apparatus according to claim 2, further comprising:
at least one of a switch and a sensor configured to actuate the air flow generating device upon insertion of the gloved hand into the unsealed hand insertion inlet.

7. The glove removal apparatus according to claim 6, wherein
the at least one of a switch and a sensor is an operator-actuated manual switch.

8. The glove removal apparatus according to claim 6, wherein
the at least one of a switch and a sensor is configured to automatically actuate the air flow generating device when the gloved hand is at least one of approaching and entering the unsealed hand insertion inlet.

9. The glove removal apparatus according to claim 1, wherein
the glove removal chamber includes left and right glove removal chambers disposed proximate one another in an arrangement which permits simultaneous removal of gloves in the respective left and right chambers.

10. A glove dispensing and removal apparatus, comprising:
an enclosed glove inflation chamber having:
a hand insertion opening at a first end of the chamber, and
a gas outlet opening at a second end of the chamber;
a plurality of gloves arranged in a stack in said chamber, each glove having an open end adjacent to said hand insertion opening and a closed end adjacent to the gas outlet opening, and each glove being secured to the stack of gloves along a portion of one side of the open end;
a gas flow generating source which communicates with said outlet opening for drawing a gas flow through the hand insertion opening, the dispensing chamber and through said gas outlet opening;
wherein said enclosed glove inflation chamber is arranged such that the gas flow generated by the gas flow generating source creates a reduced pressure in the enclosed glove inflation chamber near an outer surface of a topmost glove in said stack so as to cause the topmost glove to inflate to permit a user to insert a hand into the inflated glove;
further comprising:
an enclosed glove removal chamber having:
an unsealed hand insertion inlet at an inlet end of the chamber,
an outlet opening at an outlet end of the chamber configured to permit air within the chamber to flow out of the chamber,
wherein the unsealed hand insertion inlet is configured to provide an annular space between a gloved hand inserted into the unsealed hand insertion inlet and an inner side wall of the chamber adjacent to the unsealed hand insertion inlet such that a flow of air from the unsealed hand insertion inlet to the outlet opening configured to remove a glove from the gloved hand.

11. The glove dispensing and removal apparatus of claim 10, wherein
the glove removal chamber is structurally coupled to the glove inflation chamber.

12. The glove dispensing and removal apparatus of claim 10, wherein
the glove removal chamber is remote from the glove inflation chamber.

13. A glove dispensing and removal apparatus, comprising:
an enclosed glove inflation chamber having:
a hand insertion opening at a first end of the chamber, and
a gas outlet opening at a second end of the chamber;
a plurality of gloves arranged in a stack in said chamber, each glove having an open end adjacent to said hand insertion opening and a closed end adjacent to the gas outlet opening, and each glove being secured to the stack of gloves along a portion of one side of the open end;
a gas flow generating source which communicates with said outlet opening for drawing a gas flow through the hand insertion opening, the dispensing chamber and through said gas outlet opening;
wherein said enclosed glove inflation chamber is arranged such that the gas flow generated by the gas flow generating source creates a reduced pressure in the enclosed glove inflation chamber near an outer surface of a topmost glove in said stack so as to cause the topmost glove to inflate to permit a user to insert a hand into the inflated glove;
further comprising:
an enclosed glove removal chamber having:
an unsealed hand insertion inlet at an inlet end of the chamber,
an outlet opening at an outlet end of the chamber configured to permit air within the chamber to flow out of the chamber,
wherein the unsealed hand insertion inlet is configured to provide an annular space between a gloved hand inserted into the unsealed hand insertion inlet and an inner side wall of the chamber adjacent to the unsealed hand insertion inlet such that a flow of air from the unsealed hand insertion inlet to the outlet opening configured to remove a glove from the gloved hand while the hand is within the enclosed glove removal chamber.

* * * * *